(12) United States Patent
Berker et al.

(10) Patent No.: US 10,386,439 B2
(45) Date of Patent: Aug. 20, 2019

(54) DENSITY GUIDED ATTENUATION MAP GENERATION IN PET/MR SYSTEMS

(71) Applicant: KONINKLIJKE PHILIPS N.V., Eindhoven (NL)

(72) Inventors: Yannick Berker, Witten (DE); Shekhar Dwivedi, Willoughby Hills, OH (US); Volkmar Schulz, Wuerselen (DE); Lingxiong Shao, Saratoga, CA (US)

(73) Assignee: KONINKLIKE PHILIPS N.V., Eindhoven (NL)

( * ) Notice: Subject to any disclaimer, the term of this patent is extended or adjusted under 35 U.S.C. 154(b) by 407 days.

(21) Appl. No.: 15/104,541

(22) PCT Filed: Dec. 10, 2014

(86) PCT No.: PCT/IB2014/066765
§ 371 (c)(1),
(2) Date: Jun. 15, 2016

(87) PCT Pub. No.: WO2015/092622
PCT Pub. Date: Jun. 25, 2015

(65) Prior Publication Data
US 2016/0320466 A1 Nov. 3, 2016

Related U.S. Application Data

(60) Provisional application No. 61/918,904, filed on Dec. 20, 2013, provisional application No. 61/987,826, filed on May 2, 2014.

(51) Int. Cl.
*G01R 33/48* (2006.01)
*A61B 5/00* (2006.01)
(Continued)

(52) U.S. Cl.
CPC ..... *G01R 33/56509* (2013.01); *G01R 33/481* (2013.01); *G01R 33/4835* (2013.01);
(Continued)

(58) Field of Classification Search
CPC ............. G01R 33/181; G01R 33/4835; G01R 33/5608; G01R 33/5602; A61B 5/055; A61B 5/748; A61B 5/411; A61B 5/463
See application file for complete search history.

(56) References Cited

U.S. PATENT DOCUMENTS 6,728,334 B1   4/2004  Zhao
7,117,026 B2 * 10/2006  Shao .................. G06T 7/20
                                                    600/411
(Continued)

OTHER PUBLICATIONS

Schulz, et al., "Automatic, three-segment, MR-based attenuation correction for whole-body PET/MR data", Eur J Nucl Med Mol Imaging (2011) 38:138-1522.
(Continued)

*Primary Examiner* — Minh N Tang (57) ABSTRACT

A lung segmentation processor (40) is configured to classify magnetic resonance (MR) images based on noise characteristics. The MR segmenatation processor generates a lung region of interest (ROI) and detailed structure segmentation of the lung from the ROI. The MR segmentation processor performs an iterative normalization and region definition approach that captures the entire lung and the soft tissues within the lung accurately. Accuracy of the segmentation relies on artifact classification coming inherently from MR images. The MR segmentation processor (40) correlates segmented lung internal tissue pixels with the lung density to determine the attenuation coefficients based on the correlation. Lung densities are computed using MR data obtained from imaging sequences that minimize echo and acquisition times. The densities differentiate healthy tissues and lesions, which an attenuation map processor (36) uses to create localized attenuation maps for the lung.

20 Claims, 5 Drawing Sheets

(51) Int. Cl.
*G06K 9/46* (2006.01)
*G01R 33/565* (2006.01)
*G01R 33/56* (2006.01)
*G01T 1/16* (2006.01)
*G01T 1/164* (2006.01)
*G01R 33/483* (2006.01)
*G01R 33/50* (2006.01)
*G06T 7/11* (2017.01)
*G06T 7/136* (2017.01)
*A61B 5/055* (2006.01)

(52) U.S. Cl.
CPC ......... *G01R 33/50* (2013.01); *G01R 33/5608* (2013.01); *G01T 1/1603* (2013.01); *G01T 1/1647* (2013.01); *G06T 7/11* (2017.01); *G06T 7/136* (2017.01); *A61B 5/0035* (2013.01); *A61B 5/055* (2013.01); *G01R 33/4816* (2013.01); *G06T 2207/10088* (2013.01); *G06T 2207/20132* (2013.01); *G06T 2207/30061* (2013.01)

(56) References Cited

U.S. PATENT DOCUMENTS

| | | | |
|---|---|---|---|
| 8,165,369 | B2 | 4/2012 | Kubota |
| 8,977,027 | B2 * | 3/2015 | Da Silva ............... G06T 11/008 382/131 |
| 2010/0111386 | A1 | 5/2010 | El-Baz |
| 2010/0272341 | A1 | 10/2010 | Reeves |
| 2013/0121545 | A1 | 5/2013 | Feng |

OTHER PUBLICATIONS

Berker, et al., "MRI-Based Attenuation Correction for Hybrid PET/MRI Systems: A 4-Class Tissue Segmentation Technique Using a Combined Ultrashort-Echo-Time/Dixon MRI Sequence", J Nucl Med 2012; 53:796-804.

Berker, et al., "Out-of-field accidentals in the estimation of mean lung attenuation coefficient in PET/MR", SNMMI 2013 Annual Meeting, Vancouver, BC, Jun. 12 Scientific Paper Session: "Image Generation: Luminescence and PET/MR".

Weiger, et al., "MRI with Zero Echo Time: Hard versus Sweep Pulse Excitation", Magnetic Resonance in Medicine 66:379-389 (2011).

Marshall, et al., "Variable Lung Density Consideration in Attenuation Correction of Whole-Body PET/MRI", J Nucl Med 2012; 53:977-984.

Steinberg, et al., "Three-region MRI-based whole-body attenuation correction for automated PET reconstruction", Nuclear Medicine and Biology, vol. 37, No. 2, Feb. 1, 2010.

Hu, et al., "MR-based attenuation correction for whole-body PET/MR system". Nuclear Science Symposium Conference Record (NSS/MIC), 2010 IEEE, IEEE, Oct. 30, 2010.

Chang et al: "Investigating the use of nonattenuation corrected PET images for the attenuation correction of PET data", Medical Physics, vol. 40, No. 8, Jul. 26, 2013.

Schwenzer et al: "Pulmonary Lesion Assessment: Comparison of Whole-Body Hybrid MR/PET and PET/CT Imaging-Pilot Study", Radiology, vol. 264, No. 2, Aug. 1, 2012.

* cited by examiner

DENSITY GUIDED ATTENUATION MAP GENERATION IN PET/MR SYSTEMS

CROSS REFERENCE TO RELATED APPLICATIONS

This application is the U.S. National Phase application under 35 U.S.C. § 371 of International Application No. PCT/IB2014/066765, filed Dec. 10, 2014, published as WO 2015/092622 on Jun. 25, 2015, which claims the benefit of U.S. Provisional Patent Application No. 61/918,904 filed Dec. 20, 2013. And U.S. Provisional Patent Application No. 61/987,826 filed May 2, 2014. These applications are hereby incorporated by reference herein.

BACKGROUND

The present application relates generally to medical imaging. It finds particular application in conjunction with magnetic resonance (MR) systems, and will be described with particular reference thereto. However, it is to be understood that it also finds application in other usage scenarios and is not necessarily limited to the aforementioned application.

Imaging by emission tomography, such as positron emission tomography (PET) or single photon emission computed tomography (SPECT), is enhanced by accounting for absorption in the imaged subject using a suitable attenuation map. Emission tomography performed in combination with transmissive computed tomography (CT) advantageously benefits from the availability of radiation attenuation data provided by the CT modality. A reconstructed CT image is essentially an attenuation map of the imaged subject for the x ray radiation used in generating the CT image data. Although the x ray radiation used in CT is generally not identical with the 511 keV radiation measured in PET or the emissions measured in SPECT or other emission tomography techniques, it is known that an attenuation map for the emission tomography can be generated from the reconstructed transmission CT image by suitably scaling the CT grayscale levels to account for the differences in radiation type.

In PET, annihilation photons are attenuated and scattered by the patient's body. For attenuation and scatter correction, an attenuation map is usually required in PET. In PET/CT imaging, this can be obtained from the CT data, however in PET/MR imaging, specifically simultaneous PET/MRI, CT images are not available. The attenuation map may instead be obtained from segmented MR images where the MR images are divided into segments, and each segment is assigned a tissue class and a pre-defined attenuation coefficient. The contrast mechanism in MR is fundamentally different from that of PET or SPECT (or CT, for that matter). As a consequence, it cannot be said that a "dark" MR pixel necessarily corresponds to either high or low attenuation. For example, bone tissue and air have similar grayscale intensities for some MR imaging modes, but the attenuation of emission radiation by bone is much higher than the attenuation by air. Correct attenuation coefficients of each tissue classes are needed for accurate attenuation correction.

However, lung tissue has varying attenuation properties that vary from patient to patient. Thus, for optimal attenuation correction, the lung tissue attenuation coefficient should be estimated for each patient. For example, this can be achieved using a combination of MR image segmentation and maximum likelihood reconstruction of activity and attenuation, but this is still challenging. It has been demonstrated that there is a significant correlation between attenuation coefficients (as determined from CT data) and MRI signal intensities in a Turbo-FLASH sequence with a short echo time (TE) of 0.75 ms. It has also been hypothesized that Ultrashort-Echo-Time (UTE) imaging may reveal additional contrast or improved quantification in lung tissue: in UTE imaging, the MR signal is acquired as soon as possible (in the sub-100 µs range) after excitation to minimize the effect of extremely short signal decay times (in the order of milliseconds or sub-milliseconds in bones and lungs). For qualitative imaging of lung tissue, zero-echo time (ZTE) MR imaging has been used, both with hard pulse excitation and frequency sweep pulses.

It has been contemplated to generate an attenuation map using various techniques. In one contemplated approach, an attenuation "atlas" of a typical subject, for example of a typical human subject, is employed. The attenuation atlas identifies attenuation of various components or regions of the typical subject. However, actual subjects, such as actual human subjects, vary substantially, and it is not straightforward to adapt the attenuation atlas to a particular subject.

Further, computing accurate lung densities from MR scans is challenging. MR scans show the same signal intensity for air and bone and sometimes do not include enough signal from the lungs to generate accurate attenuation maps for the lungs. One technique requires the use of specific PET and MRI data (field of view covering and centered on the lungs; no movement of the patient to prevent motion artifacts; co-registered MRI data), which is not always available. Another approach requires a small field of view to allow for breath-hold imaging to prevent breathing motion artifacts, which impedes application of this technique in humans due to longer acquisitions times. Another approach is to use whole-body Ultrashort Echo Time imaging (UTE) to minimize echo times in an application, and use non-selective excitation pulses that can excite large regions of the patient's body combined with 3D spatial encoding and radial readout. However, using whole-body imaging can result in backfolding (i.e. wrap-around) artifacts. Alternatively, 2D UTE imaging, the selectivity of the slice-selective excitation pulse is not optimal due to constraints on pulse duration and gradient strength, impairing 2D UTE imaging performance.

Lung segmentation in MR images is important for accurate attenuation correction map generation. Detailed lung segmentation in whole body MR images for attenuation correction map generation is challenging. The presence of lesions in the lung must be considered as non-air organ, and is challenging to segment. Lung segmentation from MR images has been explored, but segmenting the lung with clear distinction of internal soft tissues and lesion poses many challenges. These challenges arise due to artefacts introduced inherently from MR scans. One potential application is to segment the soft tissues within the lungs accurately and then assign the appropriate attenuation coefficients to the segmented internal lung tissues classifying them as healthy or unhealthy. Challenges arise from inherent defects from MR scans and low resolution. Segmenting a lung as a whole for attenuation correction map generation may be incorrect if there is a lesion inside the lung.

The present application provides an innovative and adaptive approach to tune the algorithm accordingly to the MR scan and adapt a detailed segmentation based on certain parameters.

SUMMARY

In accordance with one embodiment, a lung modular system, comprising: a MRI module to scan a patient to generate MR image data. The lung modular system also includes a volume normalization module to normalize the MR image data that expands intensity values of near zero intensity pixels. The lung modular system further includes a thresholding module to generate and apply a threshold for the MR data to differentiate and separate lung pixels from non-lung pixels in a binary volume in three-dimensions. The system includes a lung region of interest (ROI) module to generate a lung ROI from the thresholded MR data; a cropping module to crop the initial volume of MR data according to the lung ROI. The system also includes a segmentation module to segment the MR data to differentiate a lung comprising at least two of lung pixels, lesion pixels, or air pixels. The system includes a density module to assess lung tissue densities for the pixels to segregate lesion pixels from lung pixels and an attenuation module to generate an attenuation map having accurate attenuation coefficients based on the segregated pixels. A classification module to classify artifacts in the MR data. A conversion module to convert a binary volume from three dimensions to two dimensional slices. The system further includes a lung box module to compute a lung box having box limits; a slice module to locate box limits for an imaging slice with a maximum pixel strength; a balancing module to balance differences between two dimensional slices; a tuning module to tune an abdomen or a trachea with respect to a lung; a mask module to create a lung mask; and a merging module to merge a two dimensional lung mask with the three dimensional binary volume.

In accordance with another embodiment, a lung segmentation system, comprising: a MR segmentation processor having a processor configured or programmed to receive a volume of magnetic resonance (MR) image data. The processor is further configured or programmed to apply a volume normalization function to the MR data to expand intensity values of near zero intensity pixels. The processor is configured or programmed to generate and apply a threshold for the MR data to differentiate and separate lung pixels from non-lung pixels in a binary volume in three-dimensions and generate a lung region of interest (ROI) from the thresholded MR data; crop the initial volume of MR data according to the lung ROI. Last, the processor is configured or programmed to segment the MR data to differentiate a lung comprising at least two of lung pixels, lesion pixels, or air pixels.

In accordance with one preferred method of the present application, a method for computing lung densities from MR images, comprising: scanning a lung region of interest using two or more echoes having different echo times to acquire MR data and processing the MR data. The method further comprises calculating lung densities from the MR data; and generating an attenuation map from the lung densities.

In accordance with one preferred method of the present application, a system to generate attenuation maps using MR images comprising: a segmentation processor having a processor configured to: segment MR images using ROI based localized segmentation accommodating for patient characteristics, image noise, artifact characteristics, and anatomical characters of a ROI. The processor is further configured to localize at least one organ lesion using density based mapping of intensity values. The processor is also configured to generate localized attenuation maps based on the density mapping and generate an ROI. The processor is configured to remove artifacts within the ROI using object tracking across localized regions wherein the object tracking is adapted according to specific MR image characteristics and patient characteristics; test the ROI for correctness; and iteratively repeat ROI generation to optimize the generated ROI.

One advantage is that localized MR based attenuation maps are generated for PET reconstruction.

Another advantage is the internal regions of the lung are segmented for lesions and normal lung tissue.

Still further advantages of the present invention will be appreciated to those of ordinary skill in the art upon reading and understand the following detailed description.

DETAILED DESCRIPTION

The present application provides for accurate attenuation coefficients for internal tissues within a lung based on lung density comparison with that of the segmented tissues. This present application provides a technique to classify each magnetic resonance (MR) scan based on noise characteristics. Noise characterization helps determine the feasibility of detailed and accurate lung segmentation. The present application provides for generating a lung region of interest (ROI) and detailed structure segmentation of the lung from the ROI. The present application provides for an iterative normalization and region definition approach that captures the entire lung and the soft tissues within the lung accurately. Accuracy of the segmentation also comes from artifact classification in MR images. The present application provides for correlating segmented lung internal tissue pixels with the lung density to determine the attenuation coefficients based on the correlation. Pixels are 2D or 3D image elements. This density based method differentiates healthy tissues and lesions.

Figure 1:
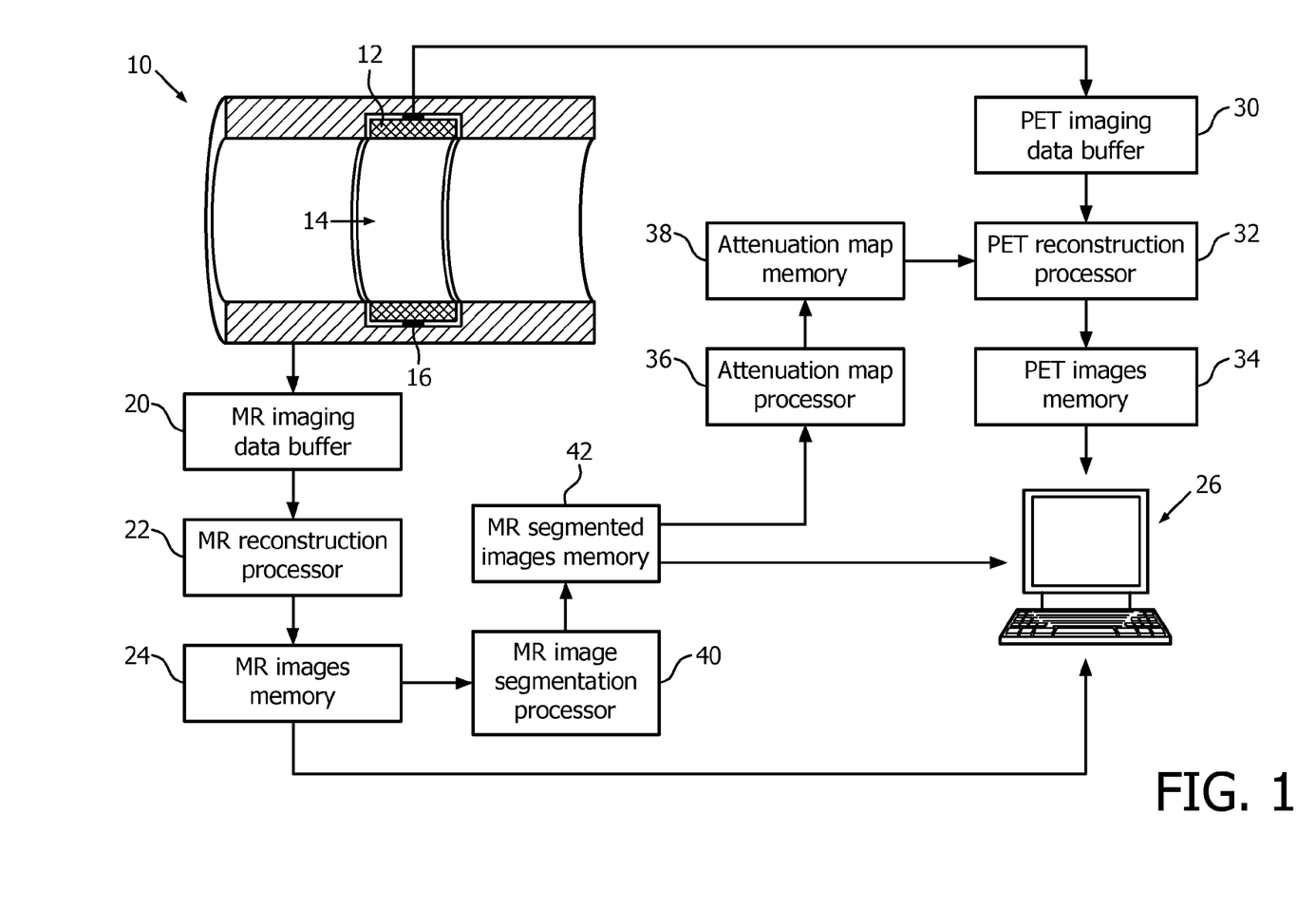
FIG. 1 diagrammatically depicts a hybrid MR/PET imaging system including a MR segmentation processor that utilizes lung densities for accurate attenuation map generation.

With reference to FIG. 1, a hybrid scanner includes a magnetic resonance (MR) scanner 10, which in the illustrated embodiment is a horizontal bore magnetic resonance scanner, and an integrated ring of nuclear imaging detectors, in one embodiment of positron emission tomography (PET) detectors 12. Both the MR scanner 10 and the integrated ring of PET detectors 12 are configured to acquire imaging data from a region of interest 14 disposed in an interior bore of the MR scanner 10. (In diagrammatic FIG. 1, the horizontal bore MR scanner 10 with integral PET detectors 12 is shown with one-half of the MR bore and the corresponding half of the ring of PET detectors 12 cut away to reveal the bore interior and the remaining half of the integrated ring of PET detectors 12). The MR scanner 10 includes components such as a main magnet for generating a static ($B_0$) magnetic field, magnetic field gradient coils for superimposing magnetic field gradients, and one or more radio frequency coils for exciting and detecting magnetic resonance, such components not being shown for simplicity in FIG. 1. The ring of PET detectors 12 includes a backbone 16 of electronics for performing selected "on-board" operations such as optionally performing analog-to-digital conversion of electrical signals caused by radiation detection events, optionally performing digital time stamping of radiation detection events, and so forth. Alternatively, some of these operations may be performed by remote electronics (not shown).

Figure 2:
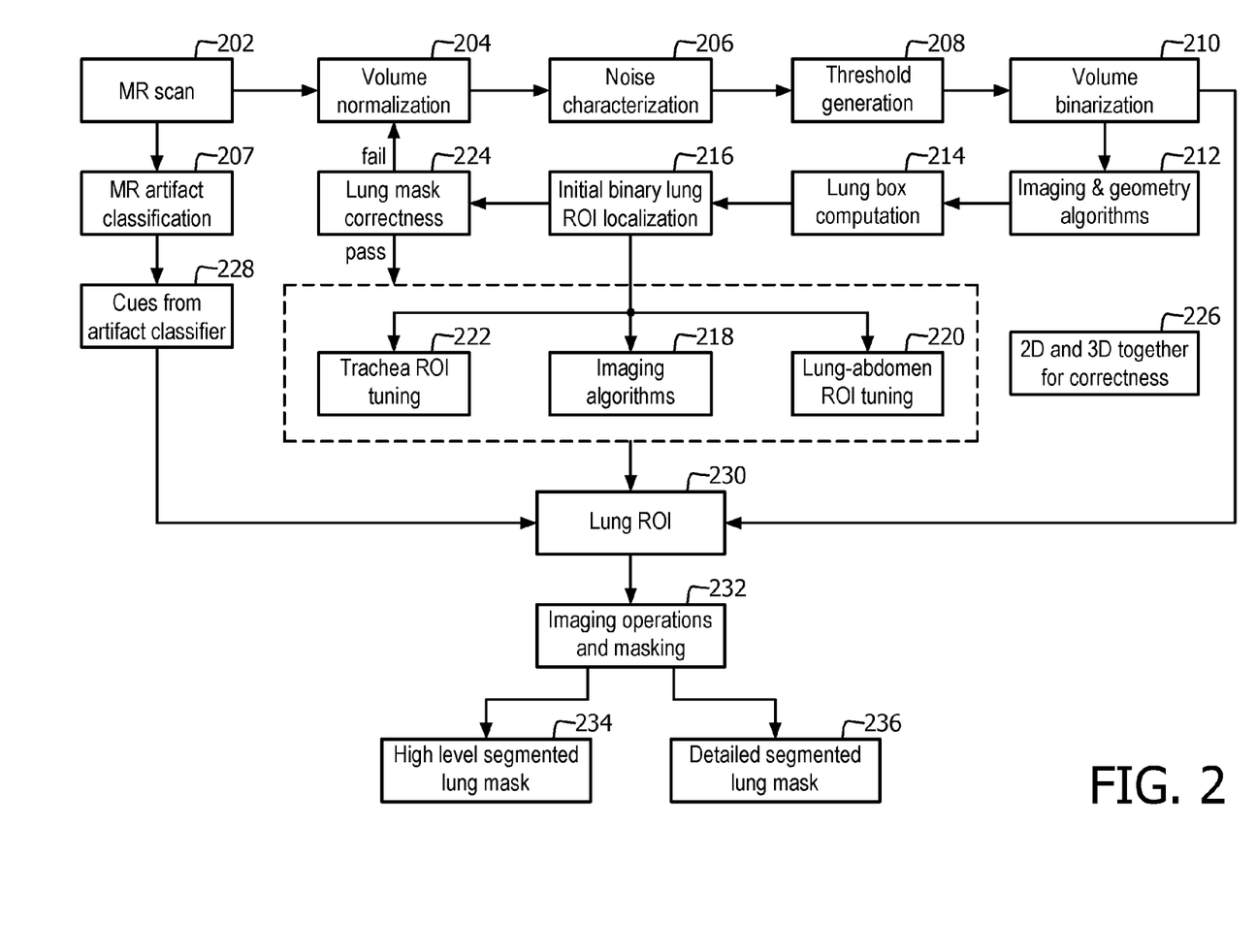
FIG. 2 depicts a modular segmentation method to segment a lung.

With continuing reference to FIG. 1 and in further reference to FIG. 2, the MR scanner 10 acquires magnetic resonance (MR) data 202, such as k-space samples, using selected spatial encoding, and the acquired MR data are stored in a MR imaging data buffer 20. An MR reconstruction processor 22 processes the MR data using a reconstruction technique comporting with the selected spatial encoding. For example, if the spatial encoding is a conventional Cartesian encoding employing slice-selective gradients during excitation and phase- and readout-encoding gradients during the magnetic resonance signal decay and readout, respectively, then the MR reconstruction processor 22 suitably employs a Fourier transform-based reconstruction technique. Other MR reconstruction techniques are also contemplated. The output of the MR reconstruction processor 22 is a MR image that is stored in an MR images memory 24 and is optionally displayed on the monitor of a computer 26 or other display device or otherwise utilized.

The PET detectors 12 and associated on-board electronics 16 and/or remote electronics (not shown) detect radiation detection events and perform energy and time windowing to identify substantially simultaneous 511 keV detection events indicative of electron-positron annihilation events. Each pair of substantially simultaneous 511 keV detection events defines a projection or line-of-response (LOR) that connects the two 511 keV detection events. This set of data, referred to as PET data or more generally as emission data, is stored in a PET imaging data buffer 30.

In some embodiments, the PET detectors 12 have sufficient temporal resolution to resolve time-of-flight time differences (or lack thereof) between the substantially simultaneous detection of two 511 keV gamma particles originating at the same electron-positron annihilation event, and the on-board and/or remote electronics are further configured to localize the electron-positron annihilation event along the line-of-response, thus generating time-of-flight PET data.

The illustrated hybrid scanner 10, 12, 16 is an example. More generally, the techniques disclosed herein for performing emission data reconstruction are suitably practiced in conjunction with any PET scanner, or still more generally in conjunction with any scanner generating emission data, such as the illustrated PET detectors 12, a stand-alone PET detector, a gamma camera generating single-photon emission computed tomography (SPECT) data, or so forth. The techniques disclosed herein for performing emission data reconstruction are further suitably practiced in conjunction with any MR image of the same subject from which the emission data are acquired, such MR image being suitably acquired by the illustrated hybrid scanner 10, 12, 16, or by a stand-alone MR scanner.

With continuing reference to FIG. 1, in one embodiment, a PET reconstruction processor 32 employs an iterative reconstruction technique to reconstruct the emission data acquired by the PET system 12, 16 (or more generally, by an radiation emission imaging system such as PET, SPECT, or so forth) to form a reconstructed emission image that is stored in a PET images memory 34 and optionally displayed on the computer 26 or another display device or otherwise utilized. To perform the emission image reconstruction, the PET reconstruction processor 32 employs an attenuation map that accounts for emission losses caused by re-absorption of emitted radiation within the subject. The attenuation map is generated by the attenuation map processor 36 and stored and accessed through the attenuation map memory 38.

The MR image is segmented by an MR image segmentation processor 40 to identify one or more geometrical regions of the subject, and this geometrical information is suitably stored in an MR segmented images memory 42. The MR segmentation processor 40 accesses a volume of MR images of a patient. The MR segmentation processor 40 performs a volume normalization 204 of the MR images to differentiate between lung and non-lung regions in the MR images. The volume normalization is a normalization function such that the pixel intensities in the MR image data have lung pixels with intensities of zero or close to zero and non-lung pixels with high intensities. The volume normalization captures as many pixels related to lungs as possible. The volume normalization adapts a function which retains most of the pixels close to 0, e.g. lung pixels, and gives a uniform value for higher intensity pixels. The volume normalization functions can also compress intensity values of higher intensity pixels. For example, an "arccot" or "arctan" normalization function helps localize the background and the lungs effectively in the thresholding step. In one embodiment, the intensity value of each pixel obtained from the normalization function is multiplied by a constant factor and used as the normalized pixel value. The volume normalization function can be adapted based on unique patient characteristics.

The MR segmentation processor 40 performs a noise characterization technique 206 on the lung pixels. The noise characterization technique has increased sensitivity to capture lung regions and soft tissues within the lung. The noise characterization technique analyzes the ratio of the number of non-zero pixels in the MR volume before and after the MR segmentation processor 40 performs the volume normalization. The ratio increases when more noise exists and helps in deciding the level of details that are adapted during lung segmentation.

The MR segmentation processor 40 performs a MR artifact classification 207 to classify artifacts like motion or aliasing or any other artifact. The artifacts have distinct characteristics and can be classified in the incoming MR data using an artifact adaption methodology and takes care while segmenting internal organs within the lungs.

Figure 3:
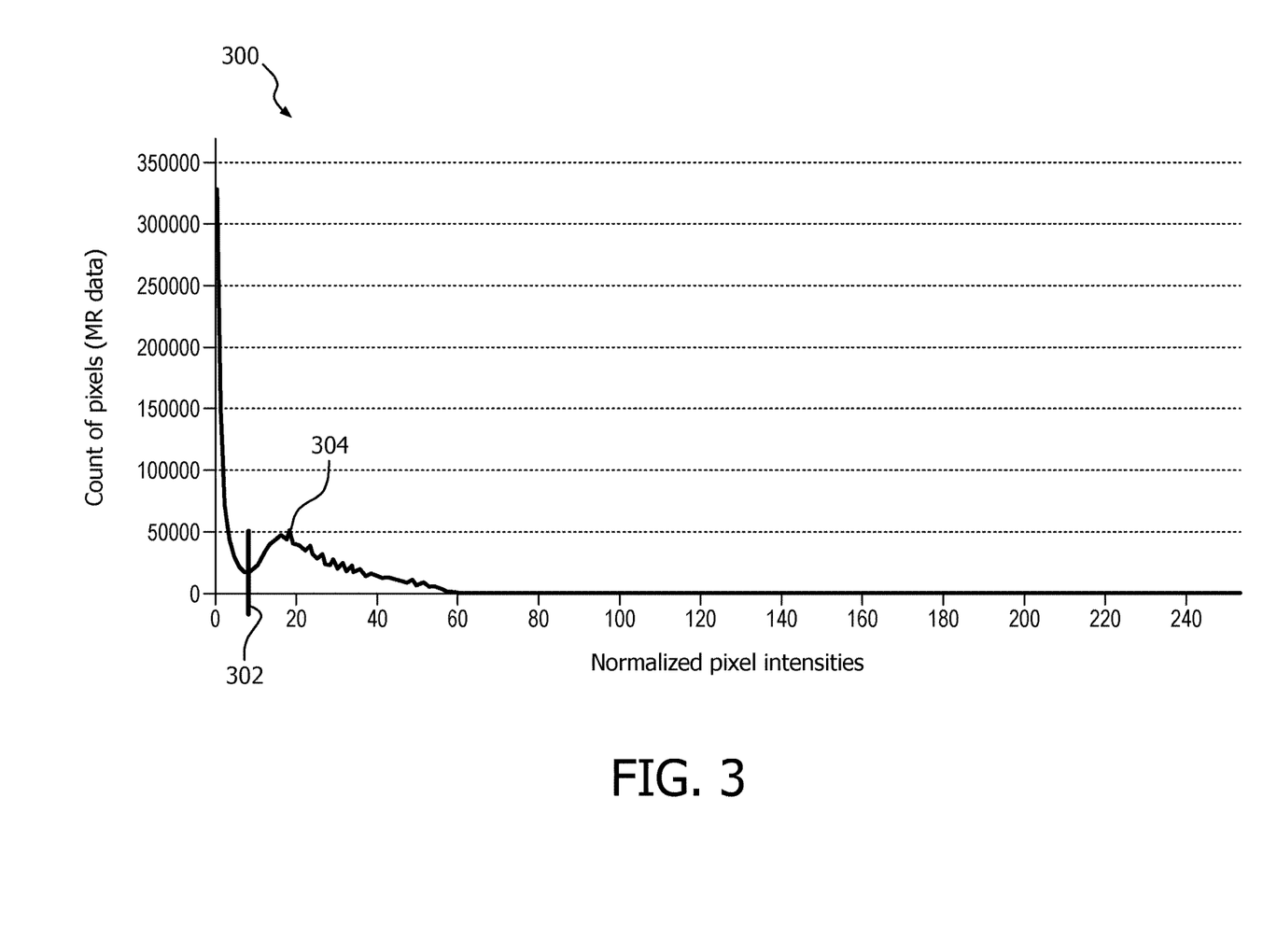
FIG. 3 depicts histogram plot of normalized pixel intensities versus count of pixels.

The MR segmentation processor 40 generates a threshold 208 for the normalized pixel intensities. A histogram of the pixel intensities is used to generate an upper and lower intensity threshold for determining between lung and non-lung pixels. With reference to FIG. 3, a generated histogram 300 plots normalized pixel intensities (x-axis) versus number of pixels (y-axis). The threshold value 302 shows the boundary between pixels counted as lung pixels (left of the threshold value 302) and pixels counted as background (right of the threshold value 302). In one embodiment, all the background pixel intensities are normalized to 255 after normalization. The non-air and non-background pixels acquire a uniform value and the histogram plots helps in determining an efficient threshold. The first rise 304 after the fall in the histogram signifies the separation of background and air pixels with rest of the intensities in the MR scan. The background pixel count (0) is not used in the histogram as its count is high, i.e. coming from non-zero background. The threshold value 302 in the histogram plot is the threshold that is automatically generated from the valley location in the plot.

The MR segmentation processor 40 applies the threshold to the MR volume images to separate lung pixels from background pixels to form a binary volume in 3D 210. In one embodiment, the binary volume is generated by normalizing and thresholding in 2D. In another embodiment, a combination algorithm is used for 2D and 3D data or a localized ROI.

Performing further operations in three dimensions can lead to leakage to background or air in 3D or partial lungs. Therefore, the MR segmentation processor 40 converts 212 the binary volume in 3D to 2D for further operations. This is performed by first doing a 2D connected component analysis to find components within the MR data. In one embodiment, the 2D connected component analysis is performed using a region growing algorithm. In another embodiment, the lung is divided into several sub-ROIs having anatomical regions, outside air, or lesions overlapping with lung pixels; the sub-ROIs are then merged for further steps.

After the connected component analysis, the processor re-labels the components based on determined rules generated using patient and anatomical characteristics. The rules include the expected minimum size, i.e. number of pixels, of the object in the slice. The classification of the components based on the MR artifact classification, and the noise characterization number of the image help determine the expected size of the component. A tracking algorithm is used to select the start and end of the lungs based on rules. The processor further cleans the slices of non-lung regions.

Figure 4:
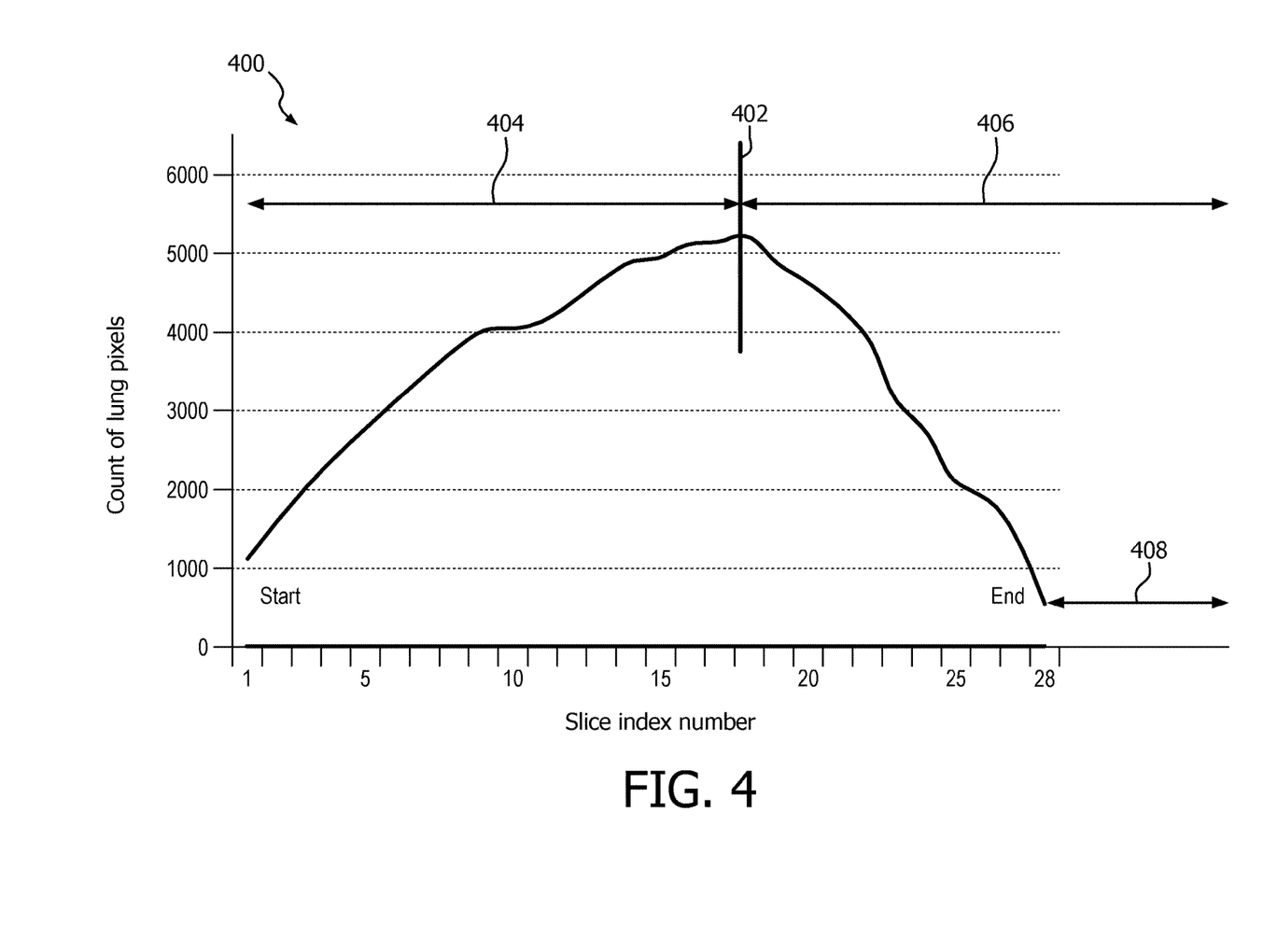
FIG. 4 depicts a plot of slices versus count of lung pixels within the slice.

The MR segmentation processor 40 generates the lung ROI by first removing the background pixels through label indexing. The background is highest in strength in all slices and the lowest in pixel intensity value. Slice wise removal does not always remove the background completely in 2D. In one embodiment, segmentation recovers the portions of lungs that were removed with segmentation in 3D. Object tracking recovers parts of the lungs if lung pixels were removed when removing the background pixels in some slices. In one embodiment, object tracking is performed in any direction in 3D. In another embodiment, object tracking is done in an axial direction across 2D slices starting from top to bottom of the lung. The MR segmentation processor 40 computes the box limits and pixel strength to form a lung box 214. The box limits are a rectangular box in the image slices that includes all non-zero pixels within the limits to form an initial lung box, i.e. the start and end of the lung ROI for a slice. The pixel strength is the count of all non-zero pixels within the box limits per slice. With reference to FIG. 4, a plot 400 of 2D slices having an index number (x-axis) versus the count of non-zero pixels, i.e. lung pixels, located within a slice (y-axis) is depicted. The MR segmentation processor 40 localizes the slice 216 having the highest pixel strength 402 and locates the box limits for the localized slice. The box limits from the localized slice having is used to generate an initial lung ROI by masking the entire MR volume, i.e. all slices, with the initial lung box. The MR segmentation processor 40 balances the difference 218 of non-zero pixels between the lung slices from the starting slice, i.e. having index number 1, of the lung to the localized slice(region 404) and the lung slices from the localized slice 402 to the end lung slice (region 406). The balancing cleans the localized slice of any bone or trachea pixels that remain in the localized slice and determines the location of the ROI to focus on for future tuning and an accurate lung ROI generation and segmentation. If the start to localized slice region 404 is larger than the localized slice to the end 406, then lung/abdomen tuning 220 is performed. If the end region 406 is larger, lung/trachea tuning 222 is performed. The lung/trachea and lung/abdomen tuning processes are automated by the processor and are iterative processes that iterate until meeting minimum size criteria. Tuning helps to accurately segment the lung pixels in overlapping regions between of lung/abdomen and lung/trachea. An overlap region 408 represents slices of the abdomen that are cleaned from the data. In some embodiment, there are more regions depending upon patient characteristics and acquisition characteristics, i.e. a truncated lung.

In one embodiment, the lung box is adaptive and uses different box sizes for ROI tuning, depending upon sub-ROIs of a particular ROI. For example trachea-lung overlap region may have smaller ROIs compared to lung ROI. Auto tuning of box limits for a particular slice in lung ROI can be determined using the box from the slice having maximum lung pixels and/or anatomical characteristics.

The initial lung box is updated with a factor in all directions to create a lung mask 224. The factor for updating the box includes noise characterization, MR artifact classification, and patient characteristics. In one embodiment, the factor is a default constant. The lung mask includes the trachea, the lung, the lung/abdomen overlap, and any portions of the lung that was removed as background. The lung mask is merged to the binary volume in 3D 226. Merging the lung mask with the 3D binary volume recovers the portion of the lung that was removed and removes any noise added by the mask. The merging creates a lung ROI 230. In one embodiment, the lung ROI is tested for correctness. If the lung ROI fails the test, the processor iterates through the previous steps until correct or optimized.

The lung ROI includes lung tissue, air, and lesions, but it is difficult to differentiate between them. The MR segmentation processor 40 segments the lung ROI 232 into internal regions. Lung segmentation segments the lung into soft tissues and air within the lung. The level of segmentation detail can be user selectable, i.e. a high level segmented lung mask 234 or a detailed segmented lung mask 236. The segmenting uses the binary mask from ROI generation to mask 232 the region within the ROI. Segmenting also includes a morphology, a connected components algorithm in all dimensions, and a relabeling algorithm. An object tracking algorithm is applied to generate the detailed lung segmentation 236. Classification from MR artefact classification is also incorporated into the segmentation to avoid segmenting noise as soft tissue within the lung.

From the internal regions, the MR segmentation processor 40 retrieves densities of the lung pixel intensities. In one embodiment, the lung densities are obtained according to an ultrashort echo time (UTE) MRI Lung Density process. The lung pixel intensities are mapped with the lung densities as intensity within the segmented regions are correlated with lung density. The lung densities help differentiate normal lung tissue and lesion tissue. From these densities, lesions are segregated from normal lung tissue therefore the attenuation map processor 36 generates more accurate attenuation coefficient maps, which are used for PET reconstruction by the PET reconstruction processor 32.

Figure 5:
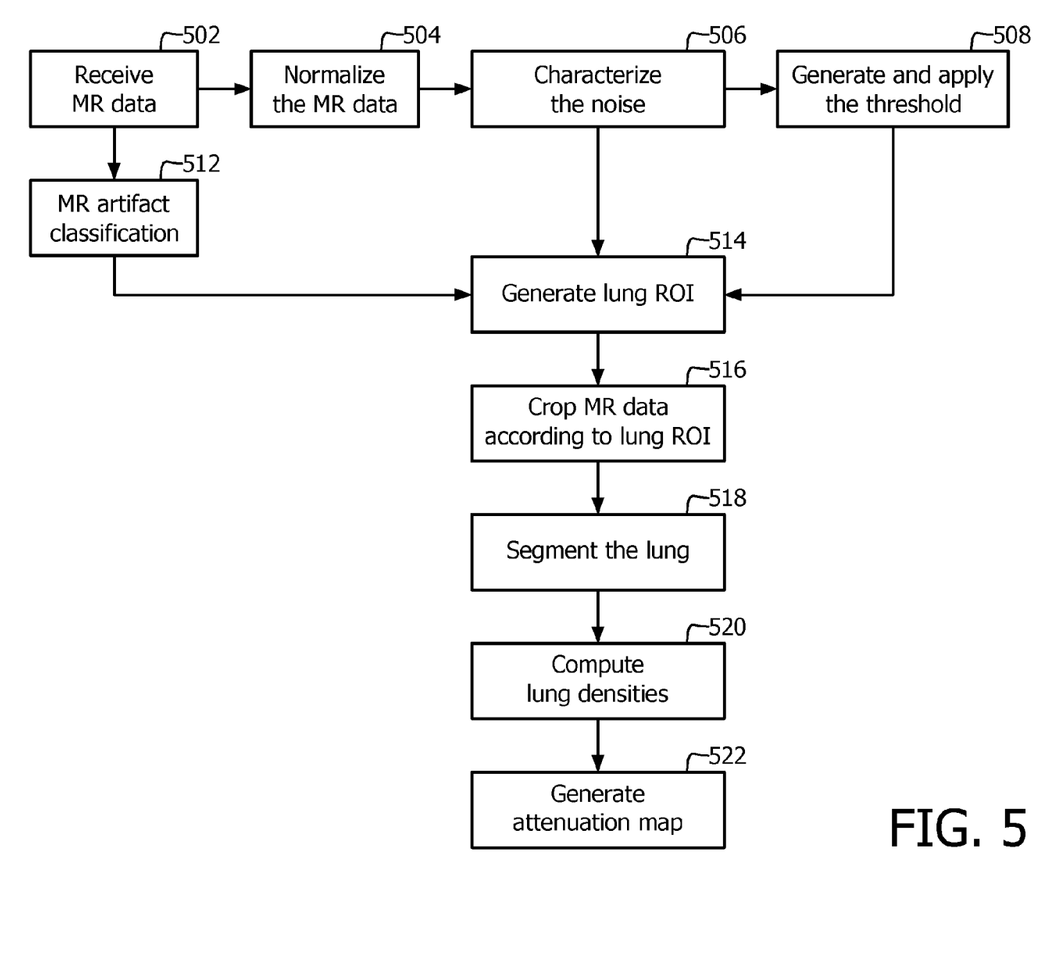
FIG. 5 depicts a lung segmentation method for accurate attenuation map generation.

With respect to FIG. 5, a method for lung segmentation to generate accurate attenuation maps is depicted. At a step 502, a patient is scanned with the MR scanner to generate a volume of MR data. At a step 504, the MR data is normalized according to a normalization function which separates lung pixels from non-lung pixels. The normalization function expands the lung intensities and contracts the non-lung intensities. At a step 506, a noise characterization technique is used to retrieve a ratio of the number of non-zero pixels in the MR data before and after the normalization. This ratio increases when more noise exists.

At a step 508, a threshold is generated and applied to the normalized intensities using a histogram plot 300. Within the histogram plot 300 the first rise of the plot 304 is used as the threshold value. When the threshold is applied, the non-lung pixels are removed from the normalized volume of MR data to generate a binary volume of three dimensional data. The pixels remaining are comprised of pixels which contain bone, abdomen, air, lesion, and lung tissue pixels.

At a step 512, artifact classification of the original MR data is performed to classify any artifacts such as motion or aliasing in the MR data. The classification can be used a factor in generating the lung ROI.

At a step 514, a lung ROI is generated using the binary volume, the MR artifact classification, and the noise characterization as described above. At a step 516, the generated lung ROI is applied to the initial volume of MR data to crop background data. At a step 518, the lung pixels are segmented. The MR artifact classification and the noise characterization help segment the internal regions of the lung as lung tissue and air.

At a step 520, lung densities are computed for the pixels within the segmented lung. The lung densities vary if the internal region of the lung is normal lung tissue or lesion. Within the normal lung tissue, density may vary. Assigning non-constant attenuation coefficients in the attenuation map solves the variation. The lesions are segregated from the rest of the lung. Computing the lung densities can be achieved using different embodiments. In one lung density computation, the patient is scanned using very short imaging times, e.g. UTE or ZTE sequences, to create more accurate lung densities. Short echo times directly correlate to accurate lung density computations because more signal is available for acquisition which reduces noise. Minimizing signal acquisition time is beneficial for receiving lung signal and results in a shortened breath hold for the patient. During MR imaging, imaging time is spent for lung attenuation imaging. This information is used for improved MR-based attenuation correction to populate the lung region of the attenuation map.

In one embodiment, the lung densities are computed from a CT-MRI calibration curve. Alternatively, a multiple-UTE sequence or a combined UTE-gradient-echo sequence is used to further determine the relative density of the lungs. For example, using two UTE echoes of 30 us and 40 us echo time. Lung densities can be computed from the ratio between lung and non-lung reference tissue. It is appreciated that the imaging of the patient can be done during step 502.

UTE Imaging is used to scan a patient in very quick intervals. In one embodiment, three-dimensional low resolution UTE is used to scan the lung region of a patient. For 3D low resolution UTE, whole body excitation can lead to undesirable artifacts such as backfolding, i.e. wraparound. Attenuation coefficients are obtained from densities using a local transmit/receive function to get localized data for the lung region. Alternatively, a local coil can be used to excite only the lung region instead of the whole body. A low resolution is used to minimize acquisition times. This allows minimization of potential artifacts.

In another embodiment, two-dimensional UTE is used to scan the patient. With 2D UTE, acquisition time is minimized using thick imaging slices of the patient which allows short excitation pulses. For example, an imaging slice with a thickness of several centimeters results in very short excitation pulses that is beneficial to lung density computation. Additionally, a low voxel resolution is used to give a fast readout of the patient. A whole body coil can be used in 2D UTE with non-specific excitation to acquire lung signals. From these scans, mean lung densities are computed over the patient lung region.

In a further embodiment, one-dimensional UTE is used to scan the patient. With 1D UTE, pencil beams are directed to the lungs of a patient to acquire a lung signal. Using pencil beams in 1D UTE gives a short echo time for computing the lung densities.

In another embodiment, a surface coil is placed over the chest region of the patient. The surface coil has a spatially limited sensitivity profile that is used to acquire a signal from lung tissue. The coil is most sensitive to tissue in the lung region when placed over the chest region of the patient.

In another embodiment, low resolution 3D Zero Echo-Time (ZTE) imaging, such as Sweep Imaging with Fourier Transformation (SWIFT) imaging, is used to obtain mean lung attenuation coefficients.

In a similar way, TZE or SWIFT MRI can be used to determine the relative proton density inside the lung due to very short echo time and response time. A UTE-short-TE-double-echo sequence can also be used by employing only a single UTE echo and a second echo with short echo time.

At a step 522, attenuation maps having accurate attenuation coefficients based on the differentiated lung tissue and lesion are created. The segmented lung and lesion tissue are reintegrated into the MR image to achieve a detailed segmented lung. The localized lesions and lung tissue are used to form localized attenuation values within the lung instead of a default constant for entire lung. The attenuation maps are used for improved PET reconstruction of the images of the patient.

It is appreciated that a user may exercise increased control of the lung segmentation by confirming automatically determined selections after some or all of the steps. As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field programmable gate array (FPGA), and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a liquid crystal display (LCD), a light emitting diode (LED) display, a plasma display, a projection display, a touch screen display, and the like.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. A lung module system, comprising:
at least one processor configured to:
normalize an MR image that expands intensity values of near zero intensity pixels and compresses intensity values of higher intensity pixels;
generate and apply a threshold for the MR image to create a thresholded MR image to differentiate and separate lung pixels from non-lung pixels in a binary volume in three-dimensions;
generate a lung region of interest (ROI) from the thresholded MR image;
crop the MR image according to the lung ROI to create a cropped MR image; and
segment the cropped MR image to differentiate a lung comprising at least two of lung pixels, lesion pixels, or air pixels to create a segmented MR image.

2. The system according to claim 1, wherein the one or more processors are further configured to:
assess lung tissue densities for pixels of the segmented cropped MR image and segregate lesion pixels from lung pixels; and
generate an attenuation map having accurate attenuation coefficients based on the segregated lesion pixels.

3. The system according to claim 2, wherein the one or more processors are further configured to:
minimize the echo time and acquisition time to compute lung tissue densities.

4. The system according to claim 2, wherein the one or more processors are further configured to:
receive positron emission tomography (PET) data;
reconstruct the PET data using the attenuation map to create an attenuation corrected PET image; and
control a display device to display the attenuation corrected PET image.

5. The system according to claim 2, wherein the one or more processors are further configured to:
compute lung tissue densities using multiple echoes for normalization.

6. The system according to claim 1, wherein the one or more processors are further configured to:
classify artifacts in the MR image;
convert the lung ROI from 3D to 2D;
generate a lung ROI shape;
balance and tune the lung ROI; and
merge at least two lung ROIs.

7. The system according to claim 1, wherein the one or more processors are further configured to:
convert the lung ROI from three-dimensions to two-dimensional slices;
compute a lung box;
compute box limits for an imaging slice; and
tune an abdomen or a trachea with respect to a lung.

8. A lung segmentation system, comprising:
one or more processors configured and programmed to:
receive a volume of magnetic resonance (MR) image data;
apply a volume normalization function to the MR image data to expand intensity values of near zero intensity pixels and compresses intensity values of higher intensity pixels to created volume normalized MR image data;
generate and apply a threshold for the volume normalized MR image data to create thresholded MR image data to differentiate and separate lung pixels from non-lung pixels in a binary volume in three-dimensions;
generate a lung region of interest (ROI) from the thresholded MR image data;
crop the MR image data according to the lung ROI to create cropped MR image data; and
segment the MR image data to differentiate a lung comprising at least two of lung pixels, lesion pixels, or air pixels to create segmented MR image data.

9. The system according to claim 8, wherein the one or more processors is further configured to:
compute a noise characterization of the volume normalized MR image data to create a normalization ratio; and
use the normalization ratio in generating the lung ROI.

10. The system according to claim 8, wherein the one or more processors is further configured to:
control a display device to display the segmented MR image data.

11. The system according to claim 8, wherein the one or more processors is further configured to perform a 2D connected component and relabeling analysis to convert a binary volume from three dimensions to two dimensional slices.

12. The system according to claim 8, wherein the one or more processors is further configured to generate the threshold using a histogram of normalized pixel intensities.

13. The system according to claim 8, wherein the one or more processors is further configured to generate the lung ROI by:
identifying a start and an end slice of the lung;
identifying a slice between the start and end slice that includes the highest number of lung pixels; and
balancing slices before the start slice and/or after the end slice to remove trachea pixels and/or abdomen pixels.

14. The system according to claim 8, wherein the one or more processors is further configured to:
assess lung tissue densities for the pixels segmented from the MR image data to segregate lesion pixels from lung pixels; and
generate an attenuation map having accurate attenuation coefficients based on the pixels segmented from the MR image data.

15. A lung segmentation method, comprising:
applying a volume normalization function to a MR image to create a normalized volume MR image of a normalized volume;
generating and applying a threshold for the normalized volume MR image to create a thresholded MR image to differentiate and separate lung pixels from non-lung pixels in a binary volume in three-dimensions;
determining a lung region of interest (ROI) from the thresholded MR image;
cropping the MR image according to the lung ROI to create a cropped MR image;
segmenting the cropped MR image to differentiate lung pixels, lesion pixels, and air pixels to create a segmented MR image.

16. The method according to claim 15, further including:
computing a noise characterization of the normalized volume to create a normalization ratio; and
using the normalization ratio as a factor in generating the lung ROI.

17. The method according to claim 15, further including:
classifying the MR image using MR artifact classification; and using the MR artifact classification as a factor in generating the lung ROI.

18. The method according to claim 15, further including:

computing lung tissue densities to segregate the lesion pixels from the lung pixels creating segregated lesion pixels and lung pixels;

generating an attenuation map having accurate attenuation coefficients based on the segregated lesion and lung pixels; and reconstructing positron emission tomography (PET) data using the attenuation map co create an attenuation corrected PET image.

19. A lung module system, comprising:

a volume normalization module configured to normalize MR image data that expands intensity values of near zero intensity pixels and compresses intensity values of higher intensity pixels;

a volume binarization module configured to generate and apply a threshold for the MR image data to create thresholded MR image data to differentiate and separate lung pixels from non-lung pixels in a binary volume in three-dimensions;

a lung region of interest (ROI) module configured to generate a lung ROI from the thresholded MR image data;

a masking module configured to crop the MR image data according to the lung ROI to create cropped MR image data; and a segmentation module segmenting the cropped MR image data to differentiate between lung pixels and non-lung pixels to create segmented MR image data.

20. The system according to claim 19, further including a display device configured to display at least one of the MR image data and the segmented MR image data.

* * * * *